(12) United States Patent
Lu et al.

(10) Patent No.: US 9,116,300 B2
(45) Date of Patent: Aug. 25, 2015

(54) MULTI-MODE INTERFEROMETER TECHNIQUES

(75) Inventors: Yanqing Lu, Nanjing (CN); Shuyi Zhang, Nanjing (CN); Qi Zhong, Jiangsu (CN); Fei Xu, Nanjing (CN); Xiaowen Lin, Nanjing (CN); Wei Hu, Nanjing (CN)

(73) Assignee: Nanjing University, Nanjing (CN)

( * ) Notice: Subject to any disclaimer, the term of this patent is extended or adjusted under 35 U.S.C. 154(b) by 866 days.

(21) Appl. No.: 13/146,308

(22) PCT Filed: Jun. 25, 2010

(86) PCT No.: PCT/CN2010/074479
§ 371 (c)(1),
(2), (4) Date: Jul. 26, 2011

(87) PCT Pub. No.: WO2011/160306
PCT Pub. Date: Dec. 29, 2011

(65) Prior Publication Data
US 2012/0224806 A1    Sep. 6, 2012

(51) Int. Cl.
*G02B 6/26* (2006.01)
*G02B 6/293* (2006.01)
(Continued)

(52) U.S. Cl.
CPC ............ *G02B 6/29344* (2013.01); *G01N 21/45* (2013.01); *G02B 6/02295* (2013.01); *G02B 6/2551* (2013.01); *G01J 2009/004* (2013.01); *G02B 6/14* (2013.01); *G02B 6/262* (2013.01)

(58) Field of Classification Search
CPC ...... G02B 6/14; G02B 6/262; G02B 6/29344; G02B 6/02295; G02B 6/2551; G01N 2/45; G01J 2009/004

USPC ................................................ 385/15, 27–28
See application file for complete search history.

(56) References Cited

U.S. PATENT DOCUMENTS 5,022,732 A * 6/1991 Engan et al. .................... 385/28
6,163,380 A 12/2000 Hays et al.
(Continued)

FOREIGN PATENT DOCUMENTS

CN     1826512 A    8/2006
CN   101650235 A    2/2010
(Continued)

OTHER PUBLICATIONS

Aref, et al. 2009 "Sensing characteristics of hollow-core photonic crystal fibre modal interferometers" 1503; 750339-1-750339-4.
(Continued)

*Primary Examiner* — Ryan Lepisto
*Assistant Examiner* — Guy Anderson
(74) *Attorney, Agent, or Firm* — Knobbe Martens Olson & Bear LLP

(57) ABSTRACT

Technologies are generally described for techniques useful in an interferometer system. In some examples, a system may include a first waveguide effective to propagate a first wave in a first mode. In some examples, the system may include a second waveguide effective to, in response to the first wave, propagate second and third waves in second and third modes, respectively. In some examples, the second waveguide may be effective to reflect the second and third waves off a reflection surface to produce first, second, third and fourth reflected waves. In some examples, the second waveguide may be effective to propagate the first and third reflected waves in the second mode and propagate the second and fourth reflected waves in the third mode.

17 Claims, 4 Drawing Sheets

(51) Int. Cl.
*G01N 21/45* (2006.01)
*G02B 6/02* (2006.01)
*G02B 6/255* (2006.01)
*G01J 9/00* (2006.01)
*G02B 6/14* (2006.01)

(56) References Cited

U.S. PATENT DOCUMENTS

| | | | |
|---|---|---|---|
| 6,643,428 | B2 | 11/2003 | Chang |
| 7,508,525 | B2 | 3/2009 | Zhou et al. |
| 2004/0246490 | A1* | 12/2004 | Wang .................... 356/479 |
| 2005/0111804 | A1* | 5/2005 | Bjarklev et al. .......... 385/125 |
| 2008/0030740 | A1* | 2/2008 | Wang .................... 356/477 |
| 2008/0037939 | A1* | 2/2008 | Xiao et al. .............. 385/96 |
| 2009/0073444 | A1* | 3/2009 | Wang .................... 356/369 |
| 2009/0091741 | A1* | 4/2009 | Dogariu ................. 356/39 |
| 2011/0235166 | A1* | 9/2011 | Zhu et al. ............... 359/341.3 |

FOREIGN PATENT DOCUMENTS

| | | |
|---|---|---|
| CN | 101655353 | 2/2010 |
| JP | 2002-537574 T | 5/2002 |
| JP | 2005-121461 A | 5/2005 |
| JP | 2006-526790 T | 11/2006 |
| JP | 2010-519557 T | 3/2010 |
| WO | WO 2005/001522 | 1/2005 |

OTHER PUBLICATIONS

Choi, et al. 2007 "All-fiber Mach-Zehnder type interferometers formed in photonic crystal fiber" *Optics Express* 15:9, 5711-5719.
Dong et al. 2010 "Temperature insensitive all-fiber compact polarization-maintaining photonic crystal fiber based interferometer and its application in fiber sensors" *Journal of Lightwave Technology* 28:7, 1011-1015.
Jha, et al. 2008 "Ultrastable in reflection photonic crystal fiber modal interferometer for accurate refractive index sensing" *Applied Physics Letters* 93 (in 3 pages).
Li, et al. 2009 "Two-mode photonic crystal fiber interferometer for temperature and strain sensing" *Asia Communications and Photonics Conference and Exhibition* 7630 (in 6 pages).
Supplementary European Search Report in European Application No. EP 10 85 3449, dated May 14, 2014 (in 5 pages).
Villatoro, et al. 2009 "Photonic crystal fiber interferometer for chemical vapor detection with high sensitivity" *Optic Express* 17: 1447-1453.
Villatoro, et al. 2009 "Photonic crystal fiber modal interferometers for accurate refractometry" *Proceedings of the Spie* 7316; 7316B-1-7316B-6.
Choi et al., "All-Fiber Mach-Zehnder Type Interferometers Formed in Photonic Crystal Fiber." Opt. Express 15 (2007): 5711-5720.
Choi et al., "Photonic Crystal Fiber Interferometer Composed of a Long Period Fiber Grating and One Point Collapsing of Air Holes." Opt. Lett. 33 (2008): 812-814.
Du et al., "Electrically Tunable Liquid-Crystal Photonic Crystal Fiber." Appl. Phys. Lett. 85 (2004): 2181-2183.
Guobin et al., "Mode Classification and Degeneracy in Photonic Crystal Fibers." Opt. Express 11 (2003): 1310-1321.
Hecht, E., Optics, International Edition, 4$^{th}$ Edition (Addison Wesley, USA, 2002): 416-421.
International Search Report and Written Opinion dated Mar. 31, 2011 in Appl. No. PCT/CN2010/074479, filed Jun. 25, 2010.
Jha et al., "Refractometry Based on a Photonic Crystal Fiber Interferometer." Opt. Lett. 34(2009): 617-619.
Jha et al., "Ultrastable in Reflection Photonic Crystal Fiber Modal Interferometer for Accurate Refractive Index Sensing." Appl. Phys. Lett. 93 (2008) 191106.
Larsen et al., "Optical Devices Based on Liquid Crystal Photonic Bandgap Fibres." Opt. Express 11 (2003): 2589-2596.
Lim et al., "Mach-Zehnder Interferometer Formed in a Photonic Crystal Fiber Based on a Pair of Long-Period Fiber Gratings." Opt. Lett. 29 (2004): 346-348.
MacPherson et al., "Remotely Addressed Optical Fiber Curvature Sensor Using Multicore Photonic Crystal Fibre." Opt. Communications 193 (2001): 97-104.
Minkovich et al., "Holey Fiber Tapers with Resonance Transmission for High-Resolution Refractive Index Sensing." Opt. Express 13 (2005): 7609-7614.
Monzon-Hernandez et al., "Photonic Crystal Fiber Microtaper Supporting Two Selective Higher-Order Modes with High Sensitivity to Gas Molecules." Appl. Phys.Lett. 93 (2008): 081106.
Villatoro et al., "Photonic-Crystal-Fiber-Enable Micro-Fabry-Perot Interferometer." Opt. Lett. 34 (2009): 2441-2443.
Villatoro et al., "Photonic Crystal Fiber Interferometer for Chemical Vapour Detection with High Sensitivity." Opt. Express 17 (2009): 1447-1453.
Villatoro et al., "Simple All-Microstructured-Optical-Fiber Interferometer Built via Fusion Splicing." Opt. Express 15 (2007): 1491.
Villatoro et al., "Temperature-Independent Strain Sensor Made From Tapered Holey Optical Fiber." Opt. Lett. 31 (2006): 305-307.
Villatoro et al., "Temperature-Insensitive Photonic Crystal Fiber Interferometer for Absolute Strain Sensing." Appl. Phys. Lett. 91 (2007): 091109.
Zhang et al., "A Three-beam Path Photonic Crystal Fiber Modal Interferometer and Its Sensing Applications." Department of Material Science and Engineering and National Laboratory of Solid State Microstructures, Nanjing University. 1-16.

* cited by examiner

MULTI-MODE INTERFEROMETER TECHNIQUES

CLAIM FOR PRIORITY

This application is the U.S. national phase entry under 35 U.S.C. §371 of PCT/CN2010/074479, filed Jun. 25, 2010, the entire disclosure of which is hereby incorporated by reference herein.

BACKGROUND

Unless otherwise indicated herein, the materials described in this section are not prior art to the claims in this application and are not admitted to be prior art by inclusion in this section.

An example interferometer system may include a light source and a mechanism or structure effective to split a light beam emitted from the light source into at least a first and a second light beam. Structures may be used to guide the first and second light beams along first and second paths. The first and second light beams, after propagating along the respective paths, may then be combined and the resulting combination may be measured. Differences in phase or amplitude between the first and second light beams in the combination may be detected and may provide information regarding characteristics of the first and second paths.

SUMMARY

In an example, a device is described. In some examples, the device may include a first waveguide and a second waveguide. In some examples, the first waveguide may be configured to operate in a first mode. In some examples, the first waveguide is effective to receive a first wave and propagate the first wave in the first mode along a first path. In some examples, the second waveguide is in optical communication with the first waveguide. In some examples, the second waveguide is configured to operate in a second mode, and a third mode. In some examples, the second waveguide includes a reflection surface. In some examples, the second waveguide is configured to receive the first wave when the first waveguide propagates the first wave. In some examples, the second waveguide is configured to, in response to the first wave, propagate a second wave in the second mode along the first path. In some examples, the second waveguide is configured to, in response to the first wave, propagate a third wave in the third mode along the first path. In some examples, the second waveguide is configured to reflect the second wave off of the reflection surface to produce a first reflected wave and a second reflected wave. In some examples, the second waveguide is configured to propagate the first reflected wave in the second mode in a second path. In some examples, the second waveguide is configured to propagate the second reflected wave in the third mode in the second path. In some examples, the second waveguide is configured to reflect the third wave off of the reflection surface to produce a third reflected wave and a fourth reflected wave. In some examples, the second waveguide is configured to propagate the third reflected wave in the third mode in the second path. In some examples, the second waveguide is configured to propagate the fourth reflected wave in the second mode in the second path.

In an example, a device is described. In some examples, the device includes a first waveguide, a second waveguide and a third waveguide. In some examples, the first waveguide is configured to operate in a first mode. In some examples, the first waveguide is effective to receive a first wave and propagate the first wave in the first mode. In some examples, a second waveguide is in optical communication with the first waveguide. In some examples, the second waveguide is configured to operate in a second mode and a third mode. In some examples, the second waveguide is effective to receive the first wave when the first waveguide propagates the first wave. In some examples, the second waveguide is further effective to, in response to the first wave, propagate a second wave in the second mode and propagate a third wave in the third mode. In some examples, the third waveguide is in optical communication with the second waveguide. In some examples, the third waveguide is configured to operate in a fourth mode and a fifth mode. In some examples, the third waveguide is effective to receive the second and third wave when the first waveguide propagates the first wave. In some examples, the third waveguide is effective to, in response to the second wave, propagate a fourth and a fifth wave in the fourth mode. In some examples, the third waveguide is effective to, in response to the third wave, propagate a sixth and a seventh wave in the fifth mode.

In some examples, a method for using a device is described. In some examples, the method includes receiving a first wave at a first waveguide. In some examples, the method includes propagating the first wave through the first waveguide in a first mode. In some examples, the method includes receiving the first wave at a second waveguide. In some examples, the second waveguide is in optical communication with the first waveguide, and the second waveguide includes a reflection surface. In some examples, the method includes, in response to the first wave, propagating a second wave in a second mode along a first path in the second waveguide. In some examples, the method includes, in response to the first wave, propagating a third wave in a third mode along the second path in the second waveguide. In some examples, the method includes reflecting the second wave off of the reflection surface to produce a first reflected wave and a second reflected wave. In some examples, the method includes propagating the first reflected wave in the second mode in a second path in the second waveguide. In some examples, the method includes propagating the second reflected wave in the third mode in the second path in the second waveguide. In some examples, the method includes reflecting the third wave off of the reflection surface to produce a third reflected wave and a fourth reflected wave. In some examples, the method includes propagating the third reflected wave in the third mode in the second path in the second waveguide. In some examples, the method includes propagating the fourth reflected wave in the second mode in the second path in the second waveguide.

In some examples, a method for using a device is described. In some examples, the method includes receiving a first wave at a first waveguide. In some examples, the method includes propagating the first wave through the first waveguide in a first mode. In some examples, the method includes receiving the first wave at a second waveguide. In some examples, the second waveguide is in optical communication with the first waveguide. In some examples, the method includes, in response to the first wave, propagating a second wave in a second mode in the second waveguide. In some examples, the method includes in response to the first wave, propagating a third wave in a third mode in the second waveguide. In some examples, the method includes receiving the second wave and third wave at a third waveguide. In some examples, the third waveguide is in optical communication with the second waveguide. In some examples, the method includes, in response to the second wave, propagating a fourth and a fifth wave in a fourth mode in the third waveguide. In some examples, the method includes in response to the third wave, propagating a sixth and a seventh wave in a fifth mode in the third waveguide.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1:
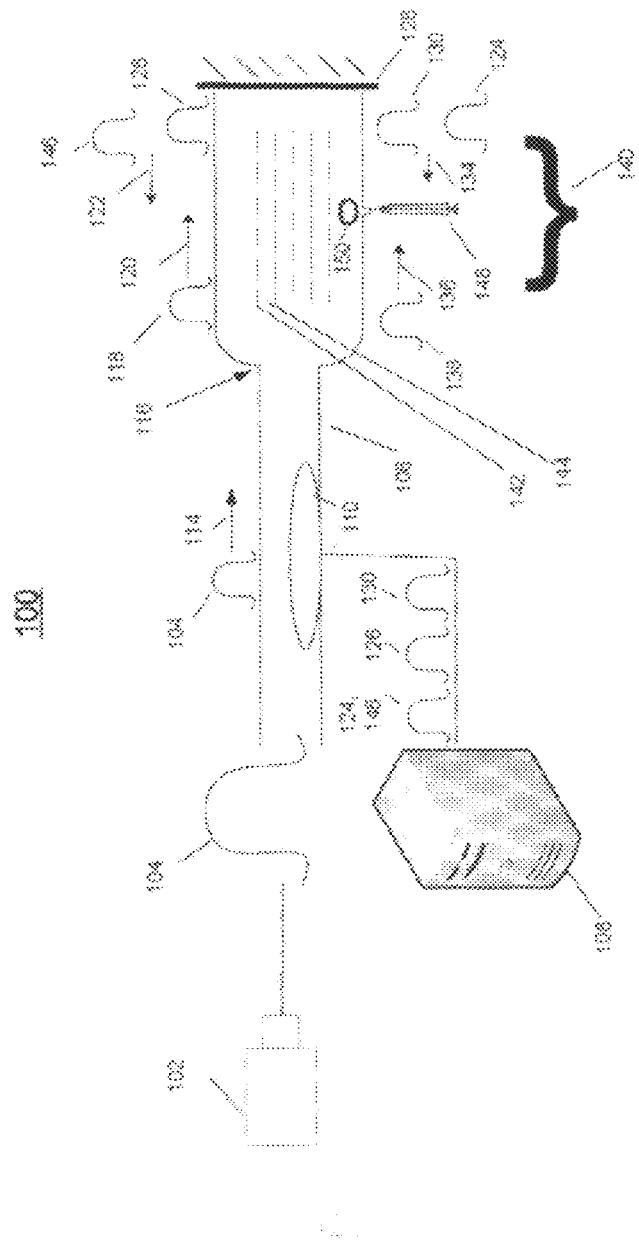
FIG. 1 illustrates some example techniques that can be utilized in a multi-mode interferometer system.

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, and devices, related to multi-mode interferometer techniques.

Briefly stated, technologies are generally described for techniques useful in an interferometer system. In some examples, a system may include a first waveguide effective to propagate a first wave in a first mode. In some examples, the system may include a second waveguide effective to, in response to the first wave, propagate second and third waves in second and third modes, respectively. In some examples, the second waveguide may be effective to reflect the second and third waves off a reflection surface to produce first, second, third and fourth reflected waves. In some examples, the second waveguide may be effective to propagate the first and third reflected waves in the second mode and propagate the second and fourth reflected waves in the third mode.

FIG. 1 illustrates some example techniques that can be utilized in a multi-mode interferometer system in accordance with at least some embodiments described herein. In some examples, an interferometer system 100 may include a light source 102, a first waveguide 106, and/or a second waveguide 140 all in optical communication. In some examples, light source 102 may be configured to output light into first waveguide 106. In some examples, first waveguide 106 is coupled to second waveguide 140. In some examples, processor 108 may be coupled to first waveguide 106 and may be configured to receive waves propagating in first waveguide 106.

In some examples, first waveguide 106 may be fusion spliced to second waveguide 140 at a fusion location 116. The fusion process may be manually controlled to maintain concentricity between first waveguide 106 and second waveguide 140. A fiber optic circulator or coupler 110 may be coupled to first waveguide 106 and may be adapted to couple waves inside first waveguide 106 to a processor 108. In some examples, processor 108 may be an optical spectrum analyzer (OSA).

In some examples, light source 102 may be a laser configured to output a light wave 104 to first waveguide 106. In an example, light source 102 may be configured to output light wave 104 with a spectral band wider than a period. For example, C-band (1.53 µm-1.57 µm), L-band (1.57 µm-1.61 µm) and/or an SLED (super-luminescent light emitting diode) source (1.3 µm to 1.5 µm) could be used. In some examples, light source 102 may be a wide-band amplified spontaneous emission (ASE) source. In some examples, first waveguide 106 may be a single mode fiber defining a first mode of propagation. In some examples, second waveguide 140 may be a photonic crystal fiber. In some examples, photonic crystal fiber 140 may include walls 142 defining holes 144. Walls 142 and holes 144 may be effective to define a second and a third mode for light waves. For example, the second and third mode may be created from walls of a different material and/or use a different index of refraction so that light waves may propagate at different velocities through photonic crystal fiber 140. In some examples, a micro-hole collapsing technique may be used where holes in second waveguide 140 may be gradually collapsed so that modes of second waveguide 140 may be transferred to a mode of first waveguide 106. For example, before splicing fibers 106 and 140, the fibers may be cleaved with a high-precision cleaver and then spliced using a fusion splicer. The holes of photonic crystal fiber 140 may collapse due to arc discharge during the fusion splicing.

In operation, in an example, a substance 150 (such as a liquid, gas or a combination of liquid and gas) may be applied into photonic crystal fiber 140 such as by an injector 148. Light source 102 may be configured to output light wave 104 to single mode fiber 106. Light wave 104 may propagate in a first mode through single mode fiber 106, through fusion location 116 and into photonic crystal fiber 140. As mentioned above, in some examples, photonic crystal fiber 140 may have two modes. In examples when light wave 104 enters photonic crystal fiber 140, light wave 104 may diffract into light waves 118 and 138. This may be due to, in part, light wave 104 diffracting from single mode fiber 106 to photonic crystal fiber 140. Light waves 118 and 138 may propagate in different paths or modes in photonic crystal fiber 140. As shown in the example, light wave 118 may propagate in a second mode (mode 2) in a path or direction 120 through photonic crystal fiber 140. As shown in the example, light wave 138 may propagate in a third mode (mode 3) in a path or direction 136 through photonic crystal fiber 140.

Light wave 118 may be incident upon an end surface 128 of photonic crystal fiber 140. In some examples, end surface 128 may be cleaved. In some examples, end surface 128 may include a surface roughness including nano-structures and/or micro-structures. Light wave 118 may reflect off of surface 128 to produce a reflected wave 126 effective to propagate back toward single mode fiber 106 in direction 122 and in mode 2. Light wave 138 may reflect off of surface 128 to produce a reflected wave 130 effective to propagate toward single mode fiber 106 in direction 134 and in mode 3. Reflected waves 126 and 130 may propagate through single mode fiber 106, be coupled into fiber optic coupler 110 and received by processor 108.

Surface 128 may be cleaved to produce a surface roughness sufficient to generate some scattering of light waves 118 and 138 and an inter-modal conversion of waves 118, 138. In an example, after light wave 118 propagates through photonic crystal fiber 140 in mode 2, and reflects off of surface 128, a portion of light wave 118 may propagate in mode 3 as shown at 124. Light wave 124 may propagate back toward single mode fiber 106 in direction 134 in mode 3. Similarly, after light wave 138 propagates through photonic crystal fiber 140 in mode 3, and reflects off of surface 128, a portion of light wave 138 may travel through mode 2 as shown at 146. Light wave 146 may propagate back toward single mode fiber 106 in direction 122 in mode 2. As the paths of light waves 124 and 146 each include a portion through mode 2 and a portion through mode 3 of photonic crystal fiber 140, light waves 124, 146 effectively create a fourth mode, mode 4. This is because, at least in part, light waves 124, 146 travel at a speed that may be the average of mode 2 and mode 3 (e.g. (mode 2+mode 3)/2). Light waves 124, 146 may be coupled into fiber optic coupler 110 and received by processor 108.

Processor 108 may be configured to determine interference among 3 different modes: 1) from wave 126 (mode 2) 2) from wave 130 (mode 3) and 3) from waves 124, 146 (mode 4). Processor 108 may be configured to determine differences such as amplitude changes, delays and/or phase shifts between any of the modes. For example, processor 108 may be configured to detect gases, chemical vapor, or volatile organic compounds 150.

In an example, in system 100 a photonic crystal fiber (PCF) large mode area (LMA)—25 from CRYSTAL FIBER could be used for photonic crystal fiber 140. In the example, photonic crystal fiber 140 may include a solid core surrounded by three rings of walls defining holes arranged in a hexagonal pattern. In the example, photonic crystal fiber 140 may have a core of approximately 25.2 µm in diameter and may have holes of an average of approximately 8.4 µm in diameter. A cladding diameter may be approximately 268 µm. An effective index of a fundamental mode may be 1.445402 and of a second mode may be 1.444549. An inter-modal index may be $8.53 \times 10^{-4}$. A length of photonic crystal fiber 140 may be approximately 26.28 cm. In an example, a single mode fiber SMF-28 106 could be used with an index of 1.444399. Processor 108 may be an ANDO AQ6370 optical spectrum analyzer.

Figure 2:
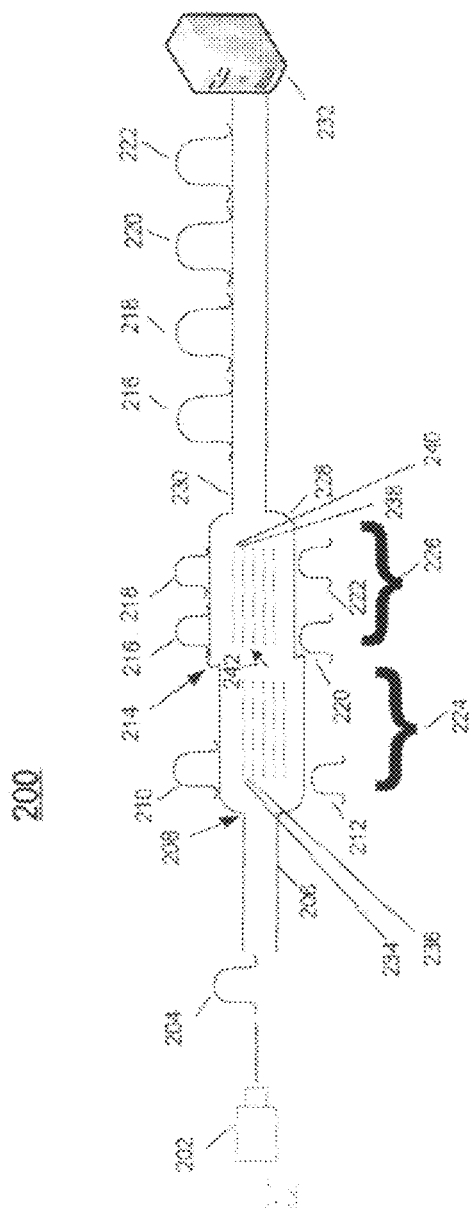
FIG. 2 illustrates some example techniques that can be utilized in a multi-mode interferometer system.

FIG. 2 illustrates some example techniques that can be utilized in a multi-modal interferometer system in accordance with at least some embodiments described herein. In some examples, an interferometer system 200 may include a light source 202, a first waveguide 206, a second waveguide 224, a third waveguide 226, a fourth waveguide 230 and/or a processor 232. In some examples, light source 202 may be configured to output light waves to first waveguide 206. Second waveguide 224 may be configured to receive light waves from first waveguide 206. Third waveguide 226 may be configured to receive light waves from second waveguide 206. Fourth waveguide 230 may be configured to receive light waves from third waveguide 226. Processor 232 may be configured to receive light waves from fourth waveguide 230.

In some examples, light source 202 may be a laser. In some examples, light source 202 may be a wide-band amplified spontaneous emission (ASE) source. In some examples, processor 232 may be an optical spectrum analyzer (OSA). In some examples, first waveguide 206 may be fusion spliced to second waveguide 224 at a fusion location 208. The fusion process may be manually controlled to maintain concentricity between first waveguide 206 and second waveguide 224. In some examples, second waveguide 224 may be fusion spliced to third waveguide 226 at a fusion location 214. In some examples, third waveguide 226 may be fusion spliced to fourth waveguide 230 at a fusion location 228. The fusion process may be manually controlled to maintain concentricity between third waveguide 226 and fourth waveguide 230.

In some examples, light source 202 may be a laser configured to output a light wave 204 to first waveguide 206. In an example, light source 202 may be configured to output light wave 104 with a spectral band wider than a period. For example, C-band (1.53 µm-1.57 µm), L-band (1.57 µm-1.61 µm) and/or an SLED (super-luminescent light emitting diode) source (1.3 µm to 1.5 µm) could be used. In some examples, first waveguide 206 and fourth waveguide 230 may be single mode fibers defining first and sixth modes of propagation respectively. In some examples, second waveguide 224 may be a photonic crystal fiber. In some examples, photonic crystal fiber 224 may include walls 234 defining holes 236. Walls 234 and holes 236 may be effective to define a second and third mode of propagation. For example, the second and third mode may be created from walls of a different material and/or use a different index of refraction so that light waves may propagate at different velocities through photonic crystal fiber 224. In an example, a micro-hole collapsing technique may be used where holes in second waveguide 224 may be gradually collapsed so that modes of second waveguide 224 may be transferred to a mode of first waveguide 206.

In some examples, third waveguide 226 may be a photonic crystal fiber of a different length than second waveguide 224. In some examples, photonic crystal fiber 226 may include walls 240 defining holes 238. Walls 240 and holes 238 may be effective to define a fourth and a fifth mode of propagation. For example, the fourth and fifth mode may be created from walls of a different material and/or use a different index of refraction so that a light waves may propagate at different velocities through photonic crystal fiber 226. In an example, a micro-hole collapsing technique may be used where holes in third waveguide 226 may be gradually collapsed so that modes of third waveguide 226 may be transferred to a mode of fourth waveguide 230.

In operation, in an example, light source 202 may be configured to output light wave 204 to single mode fiber 206. Light wave 204 may propagate through single mode fiber 206, through fusion location 208 and into photonic crystal fiber 224. As mentioned above, in some examples, photonic crystal fiber 224 may be configured to operate in two modes. In examples when light wave 204 enters photonic crystal fiber 224, light wave 204 may diffract into light waves 210 and 212. This may be due to, in part, light wave 204 diffracting from single mode fiber 206 to photonic crystal fiber 224.

Light waves 210, 212 may propagate through photonic crystal fiber 224, through fusion location 214 and into photonic crystal fiber 226. As mentioned above, in some examples, photonic crystal fiber 226 may be configured to operate in two modes distinct from the modes in photonic crystal fiber 224. For example photonic crystal fiber 224 and photonic crystal fiber 226 may have different lengths effective to create the different modes. In examples when light waves 210, 212 enter photonic crystal fiber 226, light waves 210, 212 may diffract into light waves 216, 218 and 220, 222. This may be due to, in part, photonic crystal fiber 226 being fused offset from photonic crystal fiber 224 as illustrated by arrow 242. The offset or twist may be effective to cause a mode conversion of light waves 210, 212.

Light waves 216, 218, 220, 222 may propagate through photonic crystal fiber 226, through fusion location 228, into single mode fiber 230 and be received by processor 232. Processor 232 may be configured to detect differences such as amplitude changes, delays and/or phase shifts between any of light waves 216, 218, 220, 222. For example, system 200 may be configured to detect ambient pressure based on delays and/or phase shifts.

Among other benefits, an improved sensing range may be achieved by system 100 and/or system 200. In some examples, more than two light waves may be induced and made to interfere with each other even with a two mode photonic crystal fiber. This may result in increased sensitivity and/or bandwidth range. A user using systems 100 and/or 200 may choose between increased resolution and/or sensing range. As system 100 and/or system 200 may include more than one period, greater sensing range may be achieved and shifts over even a short period may be detectable. In an example, system 100 and/or 200 could be used in miniaturized air sensing systems.

Figure 3:
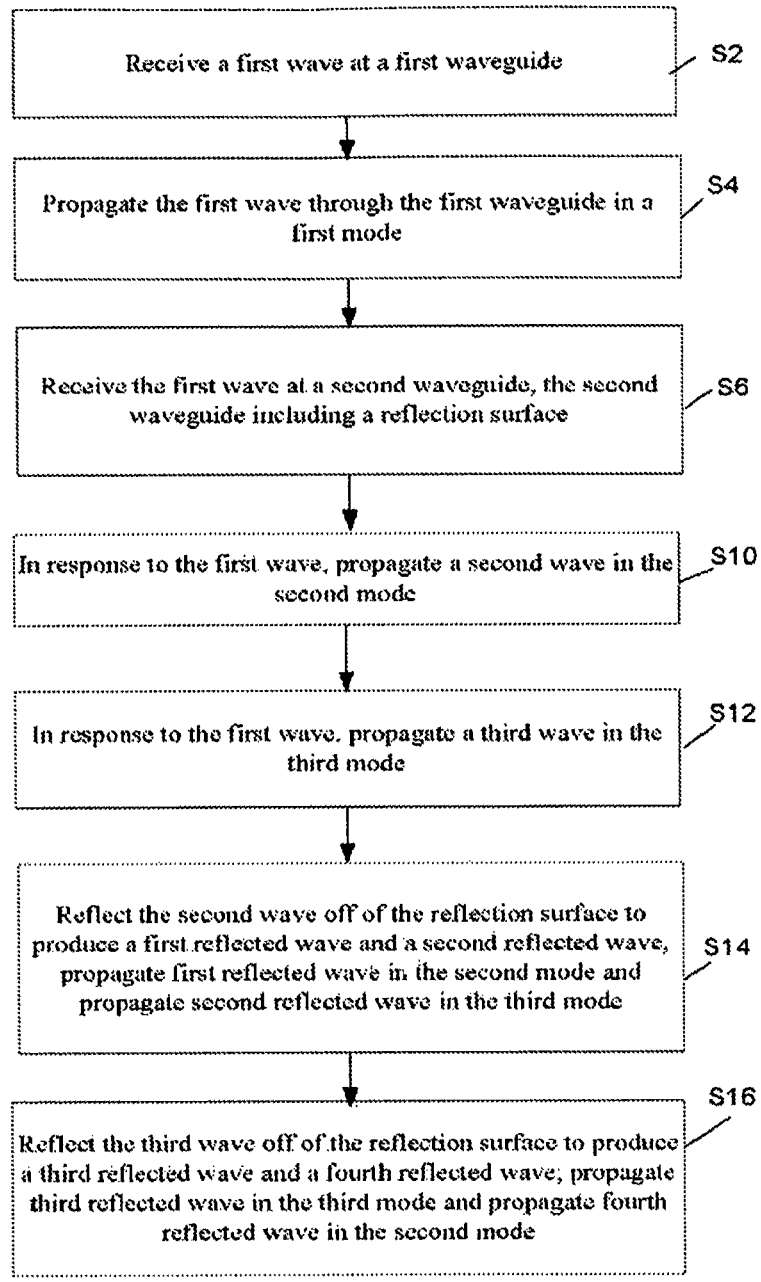
FIG. 3 depicts a flow diagram for example processes.

FIG. 3 depicts a flow diagram for example processes arranged in accordance with at least some embodiments described herein. The process in FIG. 3 could be implemented using, for example, system 100 discussed above. An example process may include one or more operations, actions, or functions as illustrated by one or more of blocks S2, S4, S6, S10, S12, S14, and/or S16. Although illustrated as discrete blocks, various blocks may be divided into additional blocks, combined into fewer blocks, or eliminated, depending on the desired implementation. Processing may begin at block S2.

At block S2, a first waveguide may be adapted to receive a first wave. Processing may continue from block S2 to block S4.

At block S4, the first waveguide may be adapted to propagate the first wave through the first waveguide in a first mode. Processing may continue from block S4 to block S6.

At block S6, a second waveguide may be adapted to receive the first wave. In some examples, the second waveguide may include a reflection surface. Processing may continue from block S6 to block S10.

At block S10, the second waveguide may be adapted to, in response to the first wave, propagate a second wave in a second mode. Processing may continue from block S10 to block S12.

At block S12, the second waveguide may be adapted to, in response to the first wave, propagate the third wave in a third mode. Processing may continue from block S12 to block S14.

At block S14, the second waveguide may be adapted to reflect the second wave off of the reflection surface to produce a first reflected wave and a second reflected wave. The second waveguide may further be adapted to propagate the first reflected wave in the second mode and propagate the second reflected wave in the third mode. Processing may continue from block S14 to block S16.

At block S16, the second waveguide may be adapted to reflect the third wave off of the reflection surface to produce a third reflected wave and a fourth reflected wave. The second waveguide may further be adapted to propagate the third reflected wave in the third mode and propagate the fourth reflected wave in the second mode.

Figure 4:
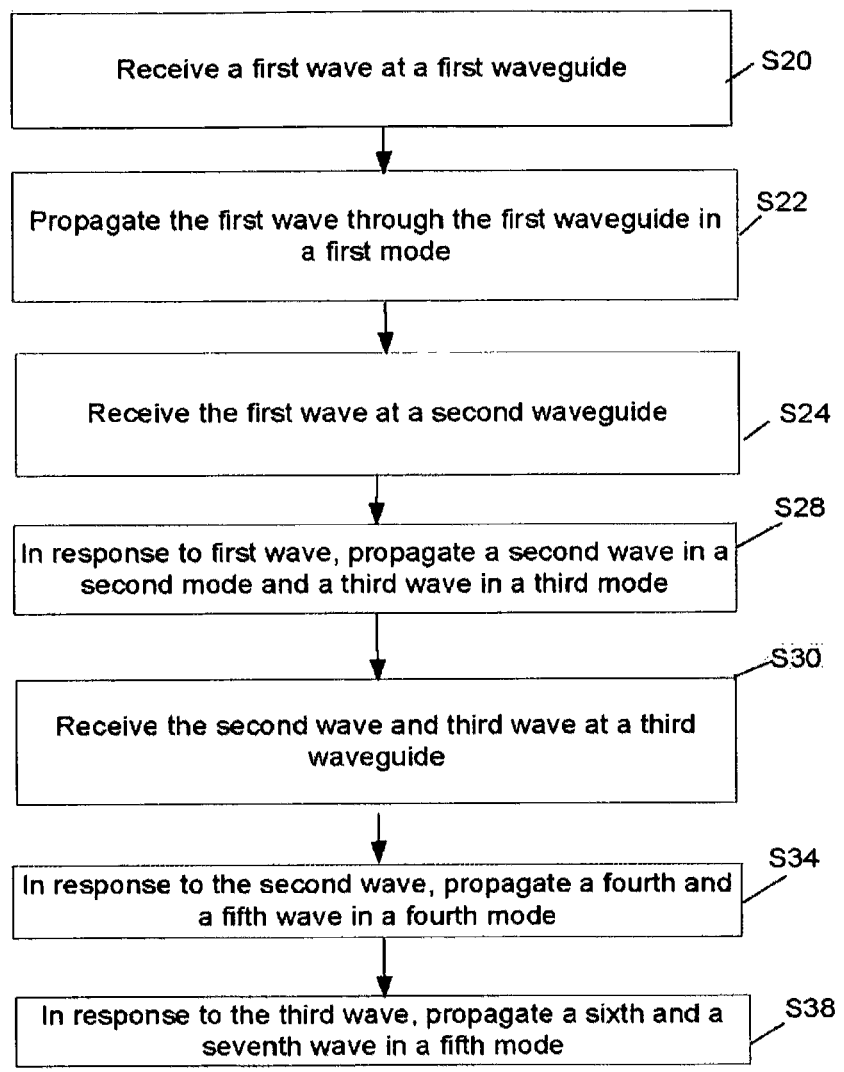
FIG. 4 depicts a flow diagram for example processes.

FIG. 4 depicts a flow diagram for example processes arranged in accordance with at least some embodiments described herein. The process in FIG. 4 could be implemented using, for example, system 200 discussed above. An example process may include one or more operations, actions, or functions as illustrated by one or more of blocks S20, S22, S24, S28, S30, S34, and/or S38. Although illustrated as discrete blocks, various blocks may be divided into additional blocks, combined into fewer blocks, or eliminated, depending on the desired implementation. Processing may begin at block S20.

At block S20, a first waveguide may be adapted to receive a first wave. Processing may continue from block S20 to block S22.

At block S22, the first waveguide may be adapted to propagate the first wave through the first waveguide in a first mode. Processing may continue from block S22 to block S24.

At block S24, a second waveguide may be adapted to receive the first wave. Processing may continue from block S24 to block S28.

At block S28, the second waveguide may be adapted to, in response to first wave, propagate a second wave in a second mode and a third wave in a third mode. Processing may continue from block S28 to block S30.

At block S30, a third waveguide may be adapted to receive the second wave and third wave. Processing may continue from block S30 to block S34.

At block S34, the third waveguide may be adapted to, in response to the second wave, propagate a fourth and a fifth wave in a fourth mode. Processing may continue from block S34 to block S38. At block S38, the third waveguide may be adapted to, in response to the third wave, propagate a sixth and a seventh wave in a fifth mode.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A device comprising:
a first waveguide configured to operate in a first mode, wherein the first waveguide is configured to receive a first wave and propagate the first wave in the first mode along a first path; and
a second waveguide in optical communication with the first waveguide, the second waveguide configured to operate in a second mode and a third mode, wherein the second waveguide includes a reflection surface, wherein the reflecting surface is configured to generate scattering of light and an inter-modal conversion of waves,
wherein the first waveguide is a single mode fiber and the second waveguide is a photonic crystal fiber, wherein the single mode fiber is coupled to the photonic crystal fiber at a fusion location, wherein the photonic crystal fiber comprises walls defining a plurality of holes, and wherein the second waveguide is configured to:
receive the first wave when the first waveguide propagates the first wave,
in response to the first wave, propagate a second wave in the second mode along the first path,
in response to the first wave, propagate a third wave in the third mode along the first path,
reflect the second wave off of the reflection surface to produce a first reflected wave and a second reflected wave,
propagate the first reflected wave in the second mode in a second path,
propagate the second reflected wave in the third mode in the second path,
reflect the third wave off of the reflection surface to produce a third reflected wave and a fourth reflected wave,
propagate the third reflected wave in the third mode in the second path, and
propagate the fourth reflected wave in the second mode in the second path.

2. The device as recited in claim 1, further comprising:
a fiber optic coupler coupled to the first waveguide; and
a processor in communication with the fiber optic coupler, wherein the processor is effective to receive the first, second, third and fourth reflected wave, and wherein the processor is configured to determine a difference between the first, second, third and fourth reflected wave.

3. The device as recited in claim 1, further comprising a light source in optical communication with the first waveguide, wherein the light source is effective to output the first wave.

4. The device as recited in claim 1, wherein at least some of the plurality of the holes defined in the walls of the photonic crystal fiber are micro-hole collapsed so that a mode of the second waveguide is transferred to a mode of the first waveguide.

5. The device as recited in claim 1, wherein the reflection surface is cleaved.

6. The device as recited in claim 1, further comprising an injector effective to inject a substance into the second waveguide.

7. The device as recited in claim 1, wherein a transition between the first and second waveguide at the fusion location is effective to split the first wave into the second and third waves.

8. A device according to claim 1, further comprising:
a third waveguide in optical communication with the second waveguide, the third waveguide configured to operate in a fourth mode and a fifth mode, the third waveguide effective to
  receive the second and third wave when the first waveguide propagates the first wave,
  in response to the second wave, propagate a fourth and a fifth wave in the fourth mode, and
  in response to the third wave, propagate a sixth and a seventh wave in the fifth mode.

9. The device as recited in claim 8, wherein:
the third waveguide is a second photonic crystal fiber.

10. The device as recited in claim 8, wherein the third waveguide is fused offset to the second waveguide.

11. The device as recited in claim 8, further comprising:
a processor in optical communication with the third waveguide, wherein the processor is effective to receive the fourth, fifth, sixth and seventh waves, and the processor is effective to determine a difference between the fourth, fifth, sixth and seventh waves.

12. The device as recited in claim 8, further comprising a light source in optical communication with the first waveguide, wherein the light source is effective to output the first wave.

13. The device as recited in claim 8, further comprising a fourth waveguide in optical communication with the third waveguide, wherein the fourth waveguide is configured to operate in a sixth mode and the fourth waveguide is effective to receive the fourth, fifth, sixth and seventh waves and propagate the fourth, fifth, sixth, and seventh waves in the sixth mode.

14. The device as recited in claim 8, wherein the second waveguide and the third waveguide have different lengths.

15. A method for using a device according to claim 1, the method comprising:
receiving a first wave at a first waveguide;
propagating the first wave through the first waveguide in a first mode;
receiving the first wave at a second waveguide, wherein the second waveguide is in optical communication with the first waveguide, and the second waveguide includes a reflection surface;
in response to the first wave, propagating a second wave in a second mode along a first path in the second waveguide;
in response to the first wave, propagating a third wave in a third mode along the second path in the second waveguide;
reflecting the second wave off of the reflection surface to produce a first reflected wave and a second reflected wave;
propagating the first reflected wave in the second mode in a second path in the second waveguide;
propagating the second reflected wave in the third mode in the second path in the second waveguide;
reflecting the third wave off of the reflection surface to produce a third reflected wave and a fourth reflected wave;
propagating the third reflected wave in the third mode in the second path in the second waveguide; and
propagating the fourth reflected wave in the second mode in the second path in the second waveguide.

16. The method as recited in claim 15, further comprising:
receiving, by a processor, the first, second, third and fourth reflected waves; and
determining, by the processor, a difference between the first, second, third and fourth reflected waves.

17. The device of claim 1, wherein the reflecting surface comprises nanostructures and/or micro-structures to achieve a surface roughness that generates scattering of light waves.

* * * * *